United States Patent [19]

Ludwig

[11] Patent Number: 4,631,116
[45] Date of Patent: Dec. 23, 1986

[54] METHOD OF MONITORING TRACE CONSTITUENTS IN PLATING BATHS

[75] Inventor: Frank A. Ludwig, Rancho Palos Verdes, Calif.

[73] Assignee: Hughes Aircraft Company, Los Angeles, Calif.

[21] Appl. No.: 741,492

[22] Filed: Jun. 5, 1985

[51] Int. Cl.[4] ........................ G01N 27/42; G01N 27/40
[52] U.S. Cl. ...................................... 204/1 T; 204/434
[58] Field of Search ........................ 204/1 T, 400, 434

[56] References Cited

U.S. PATENT DOCUMENTS

| | | | |
|---|---|---|---|
| 4,072,594 | 2/1978 | Outsuka et al. | 204/1 T |
| 4,083,754 | 4/1978 | Outsuka et al. | 204/434 |
| 4,132,605 | 1/1979 | Tench et al. | 204/195 |
| 4,146,437 | 3/1979 | O'Keefe. | |
| 4,229,264 | 10/1980 | Graunke | 204/434 |
| 4,252,027 | 2/1981 | Ogden et al. | 73/826 |
| 4,324,621 | 4/1982 | Kerby | 204/1 T |
| 4,500,391 | 2/1985 | Schmidt | 204/1 T |

OTHER PUBLICATIONS

"Cyclic Voltammetric Stripping Analysis of Acid Copper Sulfate Plating Baths" (Part 1 and 2) by R. Haak, C. Ogden & D. Tench, in *Plating and Surface Finishing*, Apr. 1981, pp. 52-55 and Mar. 1982, pp. 62-66.
Sandia Report SAND84-8815 (printed Aug. 1984), "Effect of Rhodamine-B and Saccharin on the Electric Double Layer During Nickel Electrodeposition on Platinum Studied by AC-Cyclic Voltammetry".
A. J. Bard and L. R. Faulkner, *Electrochemical Methods—Fundamentals Applications*, 1980, Chapter 9: Techniques Based on Concepts of Impedance, pp. 316-358.

*Primary Examiner*—Terryence Chapman
*Attorney, Agent, or Firm*—M. E. Lachman; A. W. Karambelas

[57] ABSTRACT

A method for monitoring the minor constituents present in a plating bath solution which affect plating deposit properties. The method involves applying a predetermined dc potential to a working electrode positioned within the plating bath solution. A constant ac signal is superimposed on the dc potential. The dc potential is varied at a predetermined rate over a predetermined range, which includes potentials which plate and strip the plating deposit. The ac current of the applied ac signal is measured between the working electrode and a counter electrode positioned within the plating bath solution as the dc potential is varied over the predetermined range. The measurement of the ac current in relation to varying dc potential is expressed as an ac current spectra or fingerprint. By optimizing all ac and dc measurement variables, spectra are obtained which contain fine structure and which enable the monitoring of minor plating bath constituents which affect plating deposit properties.

21 Claims, 13 Drawing Figures

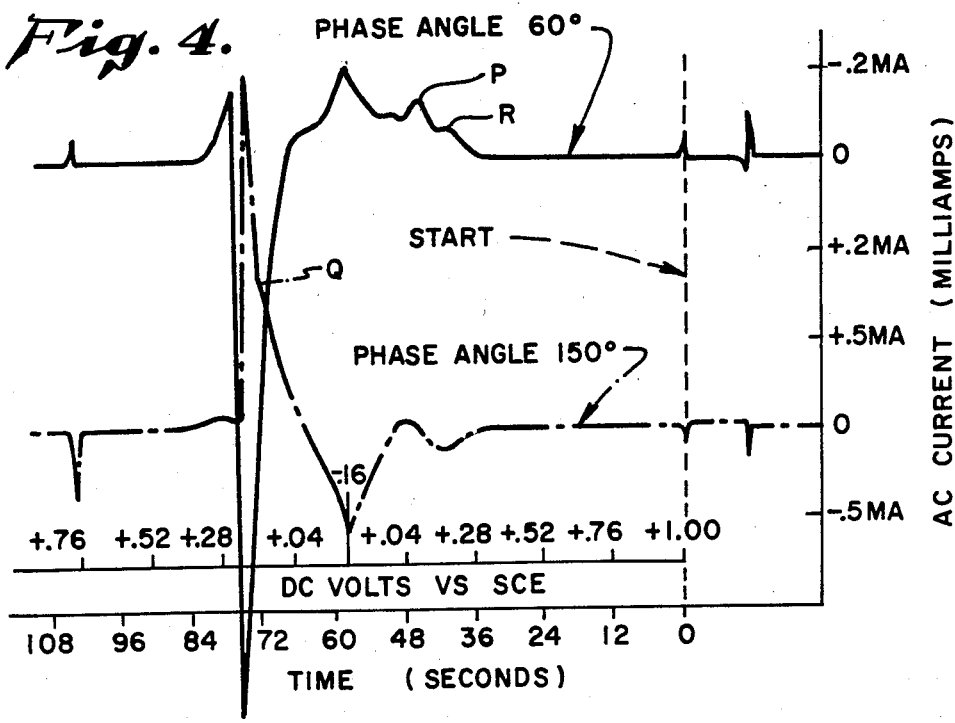
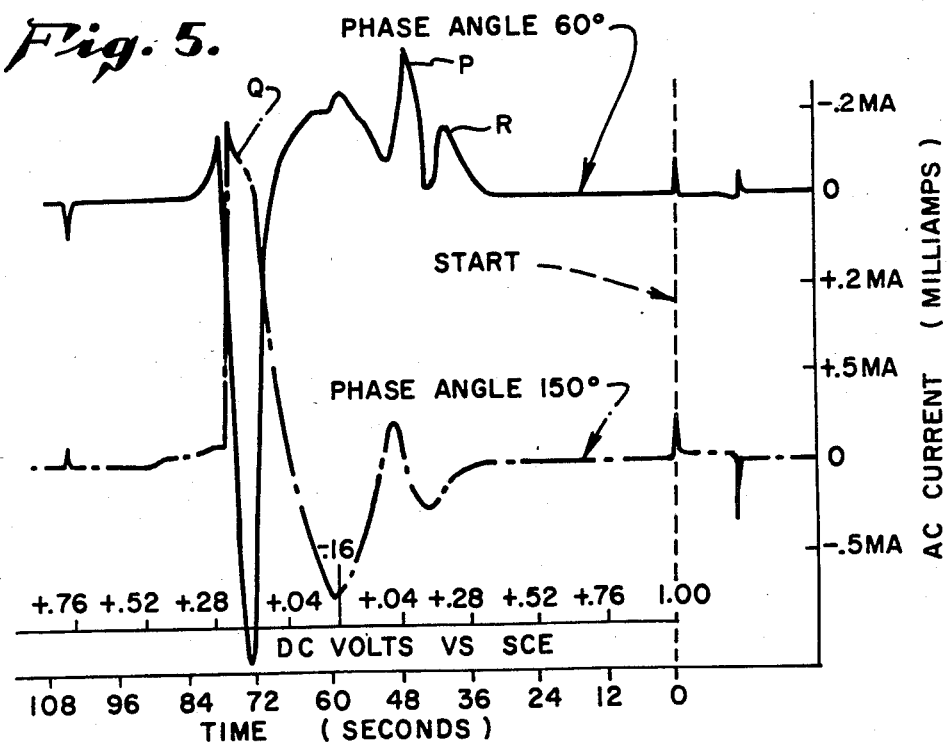

METHOD OF MONITORING TRACE CONSTITUENTS IN PLATING BATHS

BACKGROUND OF THE INVENTION

1. Field of the Invention

The present invention relates generally to plating baths and methods for monitoring the quality of the bath. More particularly, the present invention relates to an alternating current (ac) voltammetric or tensametric method that provides detailed ac current spectra or fingerprints which have unique patterns that are related to and indicative of those trace constituents in the plating bath which are known to affect plating quality of the plating baths. Use of the ac current fingerprints provides a valuable method for monitoring changes in the trace constituent make up of plating baths and evaluating plating bath quality.

2. Description of the Background Art

The important properties and characteristics of plating deposits include tensile strength, ductility, solderability, uniformity, brightness and resistance to thermal shock. These plating deposit properties are largely controlled by minor quantities of organic addition agents, their degradation products, chemical contaminants and other trace constituents which affect plating.

It is important that the plating bath be continually monitored to insure that concentrations of the trace constituents remain within limits required to achieve the desired plating deposit. The accurate control of plating deposits is especially important in the plating of copper on printed circuit boards and other electronic circuit components where the quality of the copper plating must be closely controlled. Accordingly, there has been a great deal of interest in developing methods for monitoring and controlling the levels of trace constituents in copper plating baths.

The methods presently used to monitor trace constituents in plating bath solutions include differential pulse polargraphy, cyclic voltammetric stripping, high performance liquid chromatography (HPLC) and UV fluorescence. None of these techniques has been entirely successful for a number of different reasons.

One of these methods which has been used to evaluate plating bath solutions is based on the use of cyclic voltammetry. The method is set forth in U.S. Pat. No. 4,132,605 and basically involves using a dc function generator to sweep a working electrode positioned in the bath solution through a voltammetric cycle including a metal plating range and a metal stripping range. A counter electrode is also positioned in the bath solution in series with the function generator and a coulometer is used to measure the charge of the metal stripping portion of the cycle.

The cyclic voltammetric method provides a single indirect signal which is related to the plating rate and which is useful in monitoring plating bath solutions with one or two trace constituents that affect plating rates. However, not all trace constituents and addition agents which affect plating properties also affect plating rates. Also, the addition agents for many plating baths contain two, three or four active trace constituents. Each of these active trace constituents exerts a different effect on the properties of the plated deposit. Further, the effect on plating properties of a certain concentration of these various constituents is modified by interaction with trace metal ion concentrations, trace anion concentrations and aging of the bath. Aging of the bath results in the accumulation of trace impurities and degradation products which interact and affect action of the addition agents. The numerous trace constituents present in many plating baths and the extremely complex interactions between these constituents which determines final plating deposit characteristics make the single response signal of the cyclic voltammetric technique less than adequate when close control and monitoring of the plating bath is required.

Accordingly, there is a present need to provide a simple and effective method for monitoring high quality plating baths which provides more complete and meaningful information regarding the effective concentrations of trace constituents in the plating bath. Such a method is required to provide the accurate control of plating deposit properties which is necessary for high quality plating operations.

SUMMARY OF THE INVENTION

In accordance with the present invention, a method is disclosed which provides a means for monitoring the trace constituents present at the plating surface which affect plating properties and the variations in plating characteristics caused by changes in the effective trace constituent concentrations. The method is well suited for use in monitoring high quality plating baths where complex interactions between trace amounts of both electroactive and electroinactive constituents have a major effect on plating deposit properties.

The present invention is based on the discovery that the voltammetric response of electrodes, particularly platinum electrodes, in plating bath solutions contains much more spectral fine structure than heretofore known. This fine structure is useful in providing accurate and detailed representations of the concentrations of various trace constituents in plating baths. Other methods have not been able to resolve differences in the numerous trace constituents present in plating bath or measure their concentrations. Therefore, it has not been possible in the past to relate differences in deposit properties to variations in multiple trace constituents. The method of this invention now makes possible the resolution of the trace constituents.

The method of the present invention basically involves applying a predetermined dc potential to a working electrode positioned within the plating bath. The dc potential is measured relative to a Standard Calomel Electrode (SCE). A constant ac voltage of unique frequency and amplitude is applied to or superimposed on the dc potential. The dc potential is then varied or swept at a predetermined rate over a predetermined range. The range over which the dc potential is swept includes potentials at which the metal or other substance is deposited on the working electrode and those at which the deposited material is stripped from the electrode.

During sweeping of the dc potential, the ac current resulting from the applied ac signal is measured between the working electrode and a counter electrode. The ac current is measured with respect to a reference phase angle and its quadrature angle. The changes in ac currents during the dc potential sweep are both recorded on a strip chart recorder to provide a plot of both ac currents at both phase angles vs. dc potential. These plots of variations in ac currents during dc potential sweeps provide characteristic ac current spectra or "fingerprints" for the plating bath solution and the trace constituents present therein. I found that minor variations in addition agent concentrations resulted in corresponding changes in the ac fingerprint. The ac fingerprints are therefore useful in monitoring trace constituent concentration levels.

As a feature of the present invention, the ac current fingerprint may be obtained for a plating bath which has the desired levels of addition agents and other trace constituents to produce the desired plating deposit. During plating operations, the ac fingerprint of the bath is continually measured and compared to the optimum fingerprint. Various addition agents are added from time to time to maintain the ac fingerprint of the operating bath as close to the desired fingerprints as possible. AC fingerprints may also be determined for freshly prepared plating baths and compared to an ac fingerprint for a known acceptable plating bath to insure that proper trace constituent levels are present in the new plating bath.

As another feature of the present invention, the reference phase angle (relative to the source ac signal) at which the ac current is measured can be varied to provide optimum definition and detail in the ac fingerprint. Both electroactive and electroinactive trace constituents may affect plating quality. By varying the phase angle at which the ac measurement is taken, it is possible to monitor both types of trace constituents and to monitor interactions between them which have an effect on plating properties.

As a further feature of the present invention, the ac current between the working and counter electrode may be measured at either first or second harmonic frequencies relative to the frequency of the ac signal applied to the working electrode. This feature provides an additional mode for an ac fingerprint which also is useful in characterizing and monitoring the trace constituents which affect plating quality. The second harmonic (twice the fundamental frequency) has been found to be more useful than first harmonic frequency ac signals in providing detailed spectra.

As additional features of the present invention, the frequency of the ac signal, the dc sweep rate and/or the amplitude of the ac signal may all be varied to experimentally determine which particular conditions produce a spectra having optimum detailed fingerprint structures.

The method of the present invention is an improvement over prior cyclic voltammetric dc or ac methods because the numerous peaks in the ac spectra (each having characteristic shapes and positions) provide a fingerprint or spectra of the plating bath which conveys much more detailed information and is a much more refined characterization of the trace constituents in the plating bath than the characterization which is provided by the single peak obtained by cyclic voltammetry.

Another advantage of the present invention is the ease, convenience and simplicity by which the present method lends itself to automated process control. A total analysis can be completed in two minutes with the sensing electrodes placed directly in the production plating tank. The associated electronics can be placed a reasonable distance from the production tank. Control of the analysis, analytical data storage, needed data reduction and output of analytical results can be accomplished by computer processing in essentially real time.

Another advantage of the present method is that only those trace constituents which affect plating properties are measured since the ac current is measured during a dc potential sweep which involves plating deposit and stripping. As a result, the ac fingerprint is affected by and represents only those trace constituents which affect plating properties. Since the present invention is based on electrochemical measurements, those contaminants and other substances which do not affect plating are ignored. These contaminants have been known to interfere with other conventional analytic techniques.

The above discussed and many other features and attendant advantages of the present invention will become apparent as the invention becomes better understood by reference to the following detailed description when considered in conjunction with the accompanying drawings.

BRIEF DESCRIPTION OF THE DRAWINGS

FIGS. 2-13 show exemplary ac current spectra obtained in accordance with the present invention for various acid copper plating baths having differing amounts of organic additives.

DETAILED DESCRIPTION OF THE INVENTION

Figure 1:
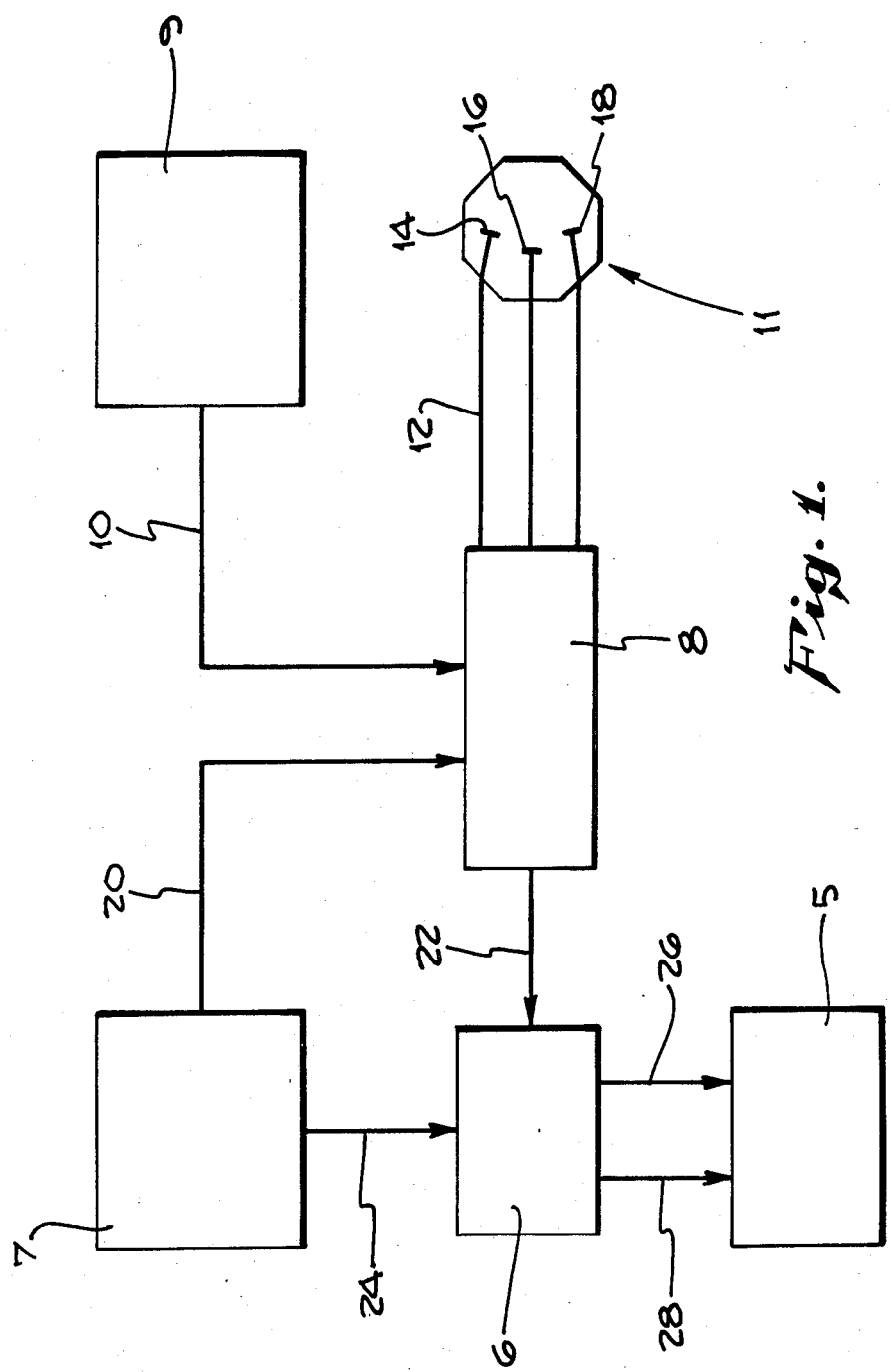
FIG. 1 is a schematic representation of a preferred embodiment for conducting the method in accordance with the present invention.

The present invention has wide application to monitoring a wide variety of plating baths. The method has application to electrowinning, electroless and electrolytic plating baths, as well as to solutions used to clean, activate or otherwise pretreat the plating substrate surface. The method is especially well-suited for monitoring metal plating baths such as those designed to deposit copper, iron, nickel, chromium, zinc, tin, gold, platinum, palladium, rhodium, silver, lead, cadmium, indium, cobalt and alloys of these metals. The following detailed description of exemplary embodiments and examples will be limited to copper plating baths, with it being understood that the invention has wide application to other plating baths in general.

Copper plating baths typically are aqueous solutions containing copper sulfate, an inorganic acid, such as sulfuric acid and a wide variety of proprietary additives. The present invention is useful in monitoring the levels of proprietary additives, degradation products of the additives and contaminants which affect plating deposits. The various additives which affect plating properties include organic additives, such as PCM Gleem, along with their degradation products and other trace contaminants. These additives and compounds are generally referred to as minor or trace constituents. For the purposes of this description, the term "trace constituents" will be considered to include these trace compounds and any other minor compounds in the plating bath which affect the plating deposit.

The present invention is based upon a method which obtains enhanced and previously unknown fine structure spectra of real and imaginary components of the complex ac impedance at a microelectrode placed into the actual plating bath solution and exposed to a limited range of both anodic and cathodic dc sweep.

The method provides a means for monitoring and analyzing the trace constituents present in a plating bath which affect the properties of the plating deposit. The method involves applying a predetermined dc potential to a working electrode positioned within the plating bath. Any of the conventional electrodes used in voltammetric analytical techniques may be used with platinum electrodes being preferred. The applied potential is measured versus a Standard Calomel Electrode (SCE), or any other convenient reference electrode. Preferably the initially applied potential is in the range where deposition of the copper plating deposit does not occur (stripping range). The dc potential is preferably varied from the stripping range potential to potentials in the plating range where copper deposition takes place and then back to the stripping potential. This cyclic dc sweep is similar to the cyclic dc sweep employed in cyclic voltammetry as set forth in U.S. Pat. No. 4,132,605 mentioned in the Background of the Invention.

Onto the dc potential is applied a small ac signal which has a prescribed peak to peak potential and frequency. The ac current between the working electrode and a counter electrode is measured with respect to a prescribed reference phase angle (and also with respect to that angle plus 90°) and plotted versus the dc potential. The counter electrode is also preferably a platinum electrode although other suitable electrodes may be used if desired.

The plots of both ac currents vs. the dc potential provides ac spectra or fingerprints which are unique for the particular trace constituent composition of the plating bath. This spectra can be compared to "known" spectra obtained from previous baths which are known to have desired plating characteristics. Also, ac spectra of plating baths during continued operation can be obtained and compared in order to monitor changes in the levels of trace constituents and the level of trace breakdown products.

Although the above-described method provides useful spectra regardless of the phase angle between the ac current and the angle at which the ac current is measured, it is preferable that the reference phase angle be varied or adjusted. Measurement of the ac current at various different reference phase angles relative to the ac signal applied to the working electrode provides a way to monitor electroactive and electroinactive trace constituents in the bath and the interaction between them. In addition, it was found that various different spectra with varying degrees of peak resolution could be obtained by measuring the ac current at different phase angles. This allows one to select various phase angles at which more complex spectra are obtained or where certain peaks in the spectra are better resolved.

In addition to making ac current measurements at various phase angles to optimize peak resolutions, it is preferred to obtain ac current measurements at second harmonic frequencies relative to the ac signal. The second harmonic measurement provides even more detail and resolution of the peak structures in some cases than possible with first harmonic frequency measurements.

A schematic diagram of an exemplary system for use in carrying out the method of the present invention is shown in FIG. 1. The system includes a dc function or waveform generator 9 which is a conventional piece of equipment designed to provide voltage sweeps or waveforms over various potential ranges at selected potential sweep rates. The function or waveform generated by the dc function generator will range for acid copper baths from about +1.1 volts to −0.2 volt vs. a Standard Calomel Electrode (SCE). The waveform generated by the dc function generator should be a potential sweep within the above ranges which has a sweep rate of 1 millivolt per second to about 500 millivolts per second. Preferably, the sweep rate for the potential will be about 20 millivolts per second. Preferably, the function generated is a slow triangular dc waveform in which the potential is varied from about +1.0 volts vs. SCE to −0.16 volt vs. SCE and back to +0.8 volts vs. SCE for copper deposition. The dc waveform generated by the function generator is input into a potentiostat 8 as represented by line 10. The potentiostat 8 is a conventional potentiostat which has the function of insuring that the potential input from the function generator is not varied due to changes in current flow through the electrochemical cell 11. The dc waveform or potential sweep is applied as represented by line 12 to a working electrode 14. The working electrode 14 is housed within a electrochemical cell 11 which also includes a standard calomel electrode 16 and a counter-electrode 18. The electrochemical cell 11 contains the plating bath solution which is being monitored. The three-electrode system (i.e., working electrode, SCE, and counter-electrode) is of the well-known type which is a conventional design commonly used in voltammetric techniques. The cell can be made as small as 2-10 cc in volume. It can also be placed inside an inverted small U-tube within the production plating tank. One end of the U-tube is placed near the plating tank cathode. A small automatically controlled pump at the apex of the U-tube pumps solution through the tube for about 30 seconds. After 10-30 seconds of quiescence, the analysis is begun. The analyzed solution in the tube is pumped back into the tank when the next analysis is started.

The system also includes a conventional ac signal or waveform generator 7 which is capable of providing a small ac signal which is input into the potentiostat 8 as represented by line 20. The potentiostat 8 is designed to superimpose the small ac signal onto the dc signal so that the dc sweep function applied to the working electrode 14 includes a superimposed ac signal. Both the ac current and dc current between the working electrode 14 and counter-electrode 18 are measured by the potentiostat 8 and transmitted to the lock-in amplifier 6 as represented by line 22. The lock-in amplifier 6 is of conventional design and is provided to selectively cancel out the dc potential and measure only the ac response to the ac signal which was superimposed on the dc function applied to the working electrode 14. A reference signal from the ac generator 7 is transmitted to the lock-in amplifier 6 as represented by line 24 so that the lock-in amplifier 6 may respond only to the chosen frequency. The output from the lockin amplifier 6 is a measure of the ac current flowing between the working electrode 14 and counter-electrode 18 during the dc potential sweep provided by the dc function generator 9. As is conventionally known, typical lock-in amplifiers provide ac current outputs mesured at the selected phase angle relative to the reference ac signal and also the ac current 90° out of phase from the selected phase angle. This feature is represented by the two lines 26 and 28 which lead from the lock-in amplifier 6 to the recorder 5. Although a lock-in amplifier is suitable which provides a single ac current measurement at a single selected phase angle, it is preferred to utilize the more conventional type lock-in amplifier in which the ac current is provided at the selected phase angle and at a phase angle 90° with respect to it.

The current measurements from the lock-in amplifier 6 are input into a strip chart recorder 5 to provide ac current spectra or fingerprints as represented in FIGS. 2-13, in which the ac current is plotted versus the dc potential sweep provided by the dc function generator.

It is preferred to vary different parameters in order to experimentally determine which conditions provide the optimum (i.e., most detailed) spectra. The following is an example of an exemplary method used to enhance or optimize the fingerprint or spectra obtained from a fresh acid copper plating bath solution to which the proper amount of addition agent has been added:

1. The first parameter to be examined is the extent of dc sweep. Though the other parameters or variables can be set over a wide range of values, the following have been found to be useful for acid copper plating bath analysis. The dc sweep rate is set at 20 mV/sec, the ac frequency is set at 50 Hz and the ac amplitude is set at 25 mV. The second harmonic mode is used and the phase angle is set at 22°, with the quadrature response at 112°. The sensitivity is set so that full scale on the ac axis of the recorder is equivalent to approximately 1–5 ma/cm$^2$ of working electrode surface area. The chart speed of the dual pen strip chart recorder is set at 10 cm/min.

The plating solution is stirred for one minute then remains quiescent for 20 seconds and then the working electrode is set at +1.5 V. vs. SCE for 10 seconds to reproducibly condition the platinum microelectrode. The sweep is then started at +1.0 volt and swept negatively until a negative voltage is reached on either the 22° or 112° trace at which a current of greater than 1 ma/cm$^2$ has been obtained. For acid copper baths this voltage is about −0.2 volt vs. SCE. The sweep direction is immediately reversed, and the sweep is retraced to +1.0 volts which is the end of the experiment.

For most acid copper plating solutions, the above procedure reveals significant spectral fine structure. By following this procedure, reproducible spectra are obtained which deviate from each other for most peaks by less than the thickness of the inked line on the strip chart plot. The sensitivity of the strip chart recorder is set so that the amplitudes of the spectra vary over the full scale of the recorder paper. Some peaks are found to have an amplitude of 1% or less of full scale while others are 60–70% of full scale. Since second harmonic spectra are second derivatives of dc sweeps, it becomes clear that large dc waves such as those due to metal deposition will have appreciable dc potential spans over which their second harmonic response is minimized. On the other hand, trace constituents will be absorbed or desorbed, oxidized or reduced over the same dc spans and will have maximum second harmonic responses. Furthermore, the metal deposition process, being a faradaic reduction process, will have maximum ac response between 0°–45° phase angle, while the addition agents which affect deposit properties partly by their strong surface active adsorption properties will have maximum ac responses at 90° phase angle, at least during those stages in which they are affecting deposit properties by means of electroinactive, non-faradaic action. It is for these reasons that dual quadrature traces are examined; because both electroactive and electroinactive effects are important to the determination of deposit properties.

While not limiting the present invention to a particular theory of operation, it is believed that the following process occurs during a dc sweep. At very positive potentials the oxide structure of the platinum surface is stabilized, and halide ion specific adsorption is stabilized. The trace amount of halide present in some plating baths is known to make a critical contribution to deposit properties and is therefore of key interest. As the sweep proceeds in the negative direction, the hydrogen pseudocapacity peaks will be observed. These peaks will be affected by various components of the plating addition agent due to the competitive adsorption taking place at the various types of platinum surface sites. Then there will be a region of metal underdeposition during which the surface is partially platinum and partially deposited metal. Peaks will appear in this region due to the knocking off from the surface of uncharged adsorbed species by the reducing cations. Also peaks will be evident due to the reduction of cations from various complex ion species. There are many additional electrodeposition subtleties and it is important to note that there is a complex interaction of many trace species contributing to deposit properties. Actual plating occurs at one potential and at one area of surface. At a different potential, depending on bath throwing power, plating may occur at other areas of the surface. All of these factors contribute to making electrodeposition phenomena a strong function of dc potential. It is reasonable, therefore, to examine ac current peaks as a function of dc potential.

Except for the original monolayer of deposition, the substrate surface is the metal being plated. For this reason, emphasis is placed on proceeding to the most negative potentials possible in the dc sweep, in order to simulate actual plating conditions by carrying on actual plating as part of the sweep. The dc sweeps are preferably taken to negative potentials where the ac first or second harmonic currents or the subsequent stripping currents are so large that they exceed the smaller peaks by a factor of about 50–100. The sensitivity of the electronic equipment shown in FIG. 1 is set high enough to pick up the spectral fine structure of these smaller peaks in the plating and stripping range. This sensitivity adjustment optimizes the measurement of the ac current in relation to the varying dc potential in order to determine the maximum spectra detail.

Since there are multiple types of sites on a plating surface and since there are numerous competitive or concurrent processes occurring at these sites during plating, the dc retrace back to positive potential is important. Previously only one or two stripping peaks were known, but in accordance with the present invention, up to seven peaks at both phase angles, or about 14 total peaks can be observed. These peaks are all distinctive and independent. The peaks can be separately related to individual variations of the various trace chemicals in the plating bath. By comparing these plated deposit peaks to the preplate peaks, the complete bath chemistry can be revealed.

2. After the furthest negative excursion of the dc sweep has been determined, the frequency is varied from 10 Hz to 10,000 Hz. The frequency that reveals the most spectral fine structure at either or both phase angles is then picked as the desired frequency.

3. The ac amplitude is then varied from 5 mV to 100 mV. If significantly more fine structure is found at a new amplitude, the frequency variation of step 2 is repeated at the new amplitude, and the new amplitude and frequency are then set.

4. Next, the dc sweep rate is varied from 1 mV/sec to 500 mV/sec. The sweep rate revealing the most fine structure is picked.

5. Next, reproducibility is confirmed by varying the electrode pre-treatment. Initial vigorous stirring must be long enough so that reasonable equilibrium conditions are obtained at the electrode surface. During this stirring period (10–80 seconds), the electrode is usually held at open circuit voltage (OCV) conditions, though this is not a requirement. For example, in some baths it is desirable to rapidly sweep from +1.1 volts to the present furthermost negative potential and back; either prior to or during stirring. The next step of the pretreatment is to allow enough quiescent time at open circuit voltage for convection from stirring to stop. Ten to 30 seconds is sufficient.

Next, the voltage and duration of the anodic pretreatment of platinum are verified. The voltage is positive to or within the stripping range. Usually 10 seconds at +1.5 volts vs. SCE is sufficient. However, when halide ion effects are important, as in many commercially available acid copper baths, then other platinum pretreatments have been found to give more reproducible halide peaks. For example, 20 seconds stirring at OCV, followed by 10 seconds quiescence at OCV followed by 10 seconds at +1.1 volts, followed by 10 seconds at 1.3 volts. After the pre-treatment the sweep is immediately started at either +1.0 or +1.1 volts in quiescent solution. Halide ion interactions with other trace addition agent peaks are minimized, while peaks unique to halide ion are stabilized by the second pretreatment procedure.

The optimum pre-treatment procedure is chosen to give maximum fingerprint reproducibility. Reproducibility is satisfactory when one spectra cannot be distinguished from the next, no matter whether the two spectra were run one immediately after the other or whether the electrode sat untended in the solution for one or more days. In many cases reproducibility is not very sensitive to the exact details of pre-treatment.

6. Next, data are obtained at a number of phase angles, for example, 0°, 22°, 45° and 60° reference phase angles and the complementary quadrature angles. The spectra are examined for fine structure which was not revealed at the initial phase angle of 22°.

7. The optimized fine structure procedure is now used to obtain or confirm the sought after correlations with deposit properties and/or addition agent and trace constituent concentrations. The various peaks can be identified and calibrated if so desired through controlled additions of known substances, or the fine structure can simply be correlated with optimum deposit properties and production yield rate. When fine structure fingerprints are not in the desired range, the bath can be filtered, carbon treated, reconstituted, dummied, etc. until a proper fingerprint is again obtained.

8. It may be found that the steps 1–7 which optimized fine structure detail for one trace constituent, did not optimize the detail for another trace constituent. Steps 1–7 must then be repeated and parameter values chosen which optimize spectral detail for the other constituent. A complete trace analysis may then require more than one determination of a spectrum.

By following the above eight steps which establish the settings of all of the ac and dc measurement variables, maximum spectra detail is obtained containing heretofore unknown fine structure.

Examples of practice are as follows:

A system as shown schematically in FIG. 1 was used to obtain ac current spectra of a Sel-Rex Cu-Bath M Special acid copper bath which included the Sel-Rex organic additives known as Lo and D. Sel-Rex copper baths are prepared using proprietary ingredients and following instructions available from Sel-Rex Division of OMI International Corp., 75 River Road, Nutley, N.J. 07110. Tests were also run on acid copper baths without any additives.

The acid copper baths were aqueous solutions prepared according to the following nominal formulation:
75 g/l $CuSO_4.5H_2O$
10 vol. percent $H_2SO_4$ (96% concentrated reagent grade)
75 ppm chloride ion
5–20 ml/gal total addition agents The specific system used in the examples included a 2.5 mm diameter spherical platinum microelectrode which was used as the working electrode. A 200 ml. beaker was filled with 150 ml of plating solution. A 2-inch long by 2-inch diameter platinum gauze electrode was used as a counter-electrode. Equally sensitive, reproducible and selective fine structure has been obtained in small cells containing 5–10 ml of solution. In addition, microelectrodes need not be spherical. Identical fine structure data have been obtained at wire electrodes (1.0 mm diameter and 1.3 cm long) which were insulated with plastic shrinkable tubing above their exposed length. The working electrode was placed in the center of the beaker and a standard calomel reference electrode (SCE) was placed between the working and counter-electrodes. It was found that the location of the reference and working electrodes in the beaker had no effect on the ac current spectra. The electrodes were connected to a PAR 173 potentiostat with a PAR 276 plug-in interface, the output of which was used as the input to a PAR 5206 lock-in amplifier. The PAR 173 potentiostat was driven with a dc signal input from a PAR 175 universal programmer and nominally, with a 25 mV, 50 Hz ac sine wave from a Wave-Tek Model 180 signal generator. The ac signal was also fed into the 5206 lock-in amplifier as the reference signal. The in-phase and quadrature ac currents were recorded as a function of dc sweep rate on a two pen strip chart recorder. These current outputs are the signal outputs obtained from the channel 1 and channel 2 outputs of the 5206 lock-in amplifier. The spectral data were obtained at a nominal 20 mV/sec triangular dc sweep rate starting at +1.0 volts vs. SCE and sweeping to −0.16 volt vs. SCE and returning to +0.8 volt. The ac current response was set at 0.20 mA/inch on the chart paper. The chart was set at 10 cm/minute, yielding 120 mV/cm on the dc axis of the chart. PAR equipment is available from Princeton Applied Research, P.O. Box 2565, Princeton, N.J. 08540 and the Wave-Tek signal generator is available from Wavetek San Diego, Inc., 9045 Balboa Avenue, San Diego, Calif. 92123.

FIGS. 2–11 are the ac second harmonic current spectra or fingerprints obtained from copper Sel-Rex baths of the type described above. The make up of the baths for each figure are as follows FIG. 2: Sel-Rex Acid Copper with 5 ml/gal total addition agent (3.75 ml/gal "D", 1.25 ml/gal "Lo"); 50 ppm Cl−; 8.9 oz/gal $CuSO_4.5H_2O$; and 27 oz/gal $H_2SO_4$.

Figure 2:
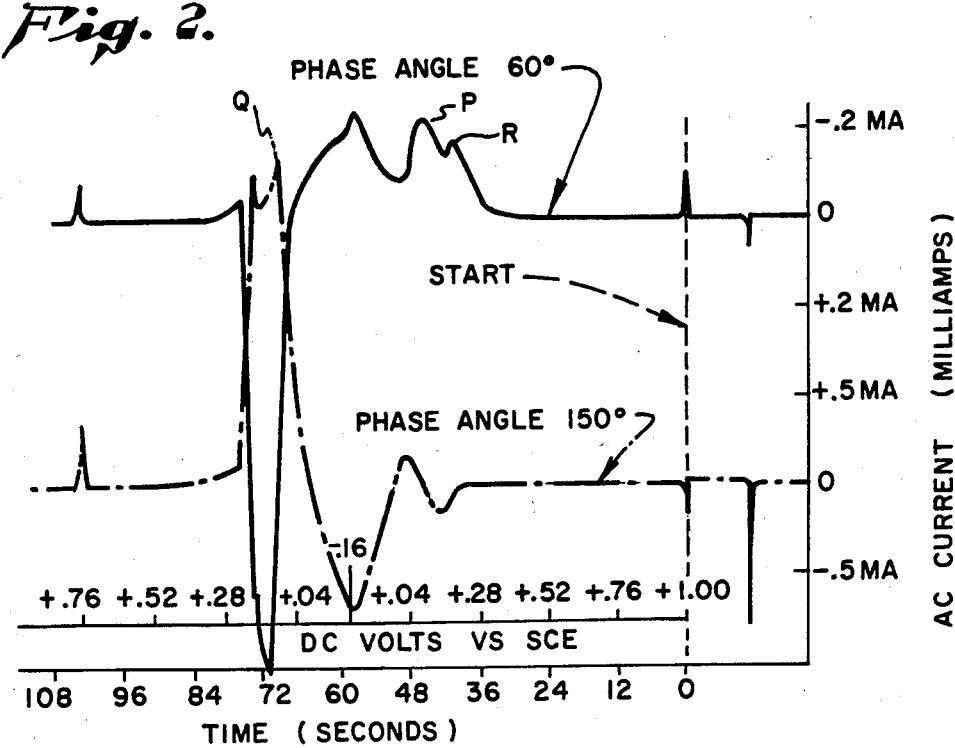
Figure 3:
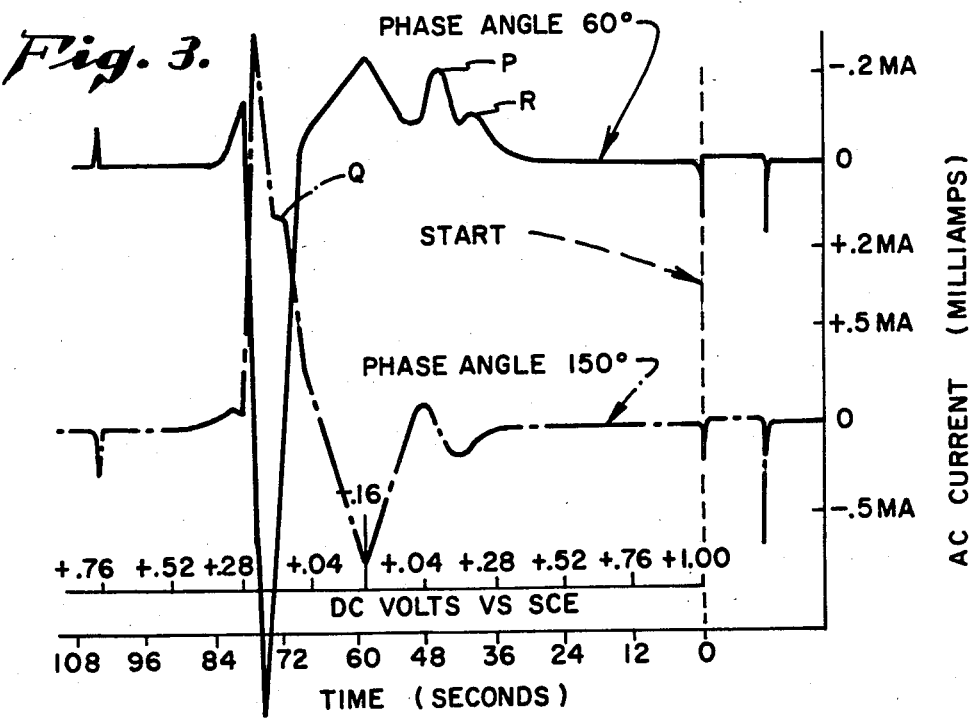

FIG. 3: Same as FIG. 2 bath except 10 ml/gal total addition agent (7.5 ml/gal "D", 2.5 ml/gal "Lo").

FIG. 4: Same as FIG. 2 bath except 20 ml/gal total (15 ml/gal "D", 5 ml/gal "Lo").

FIG. 5: Same as FIG. 2 bath except 5 ml/gal total addition agent (4 ml/gal "D", 1 ml/gal "Lo").

Figure 6:
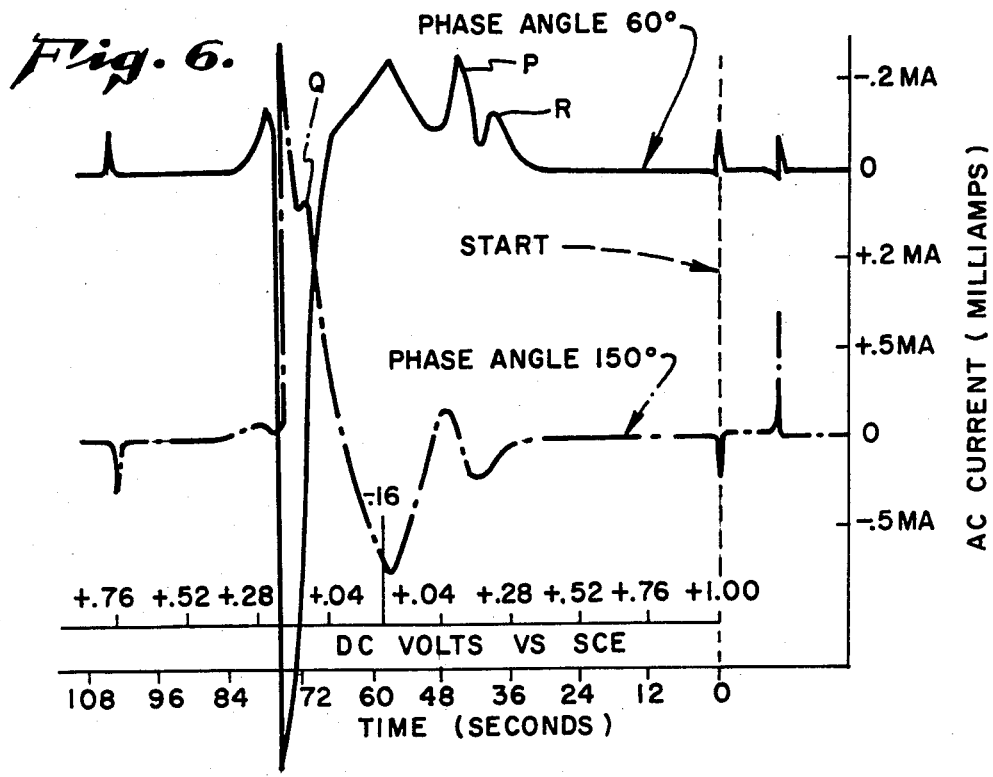

FIG. 6: Same as FIG. 2 bath except 10 ml/gal total (8 ml/gal "D", 2 ml/gal "Lo").

Figure 7:
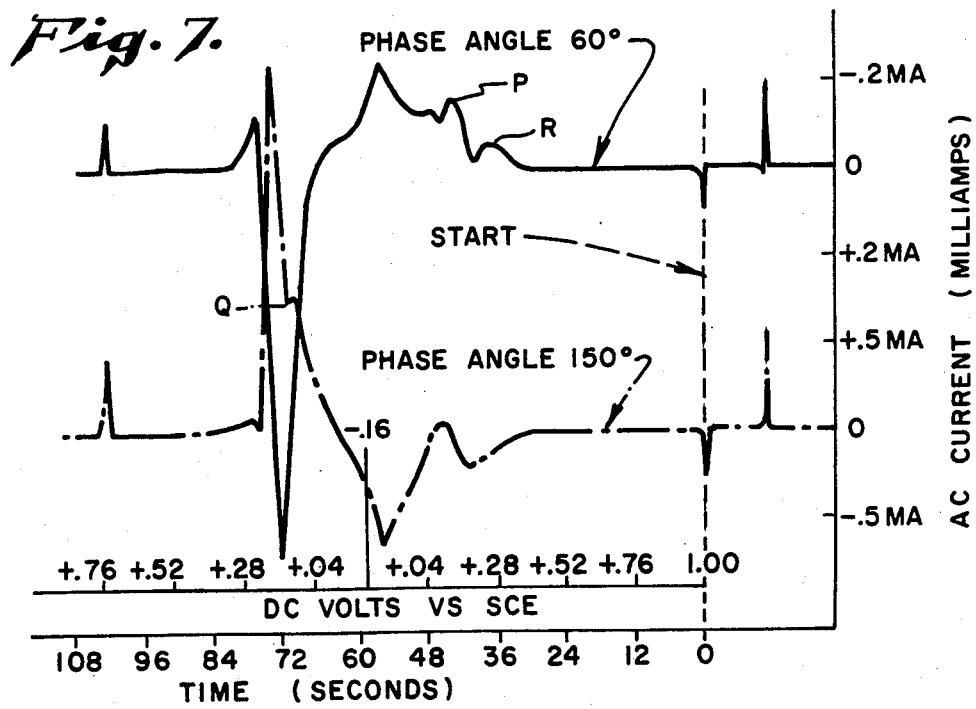

FIG. 7: Same as FIG. 2 bath except 20 ml/gal total (16 ml/gal "D", 4 ml/gal "Lo").

Figure 8:
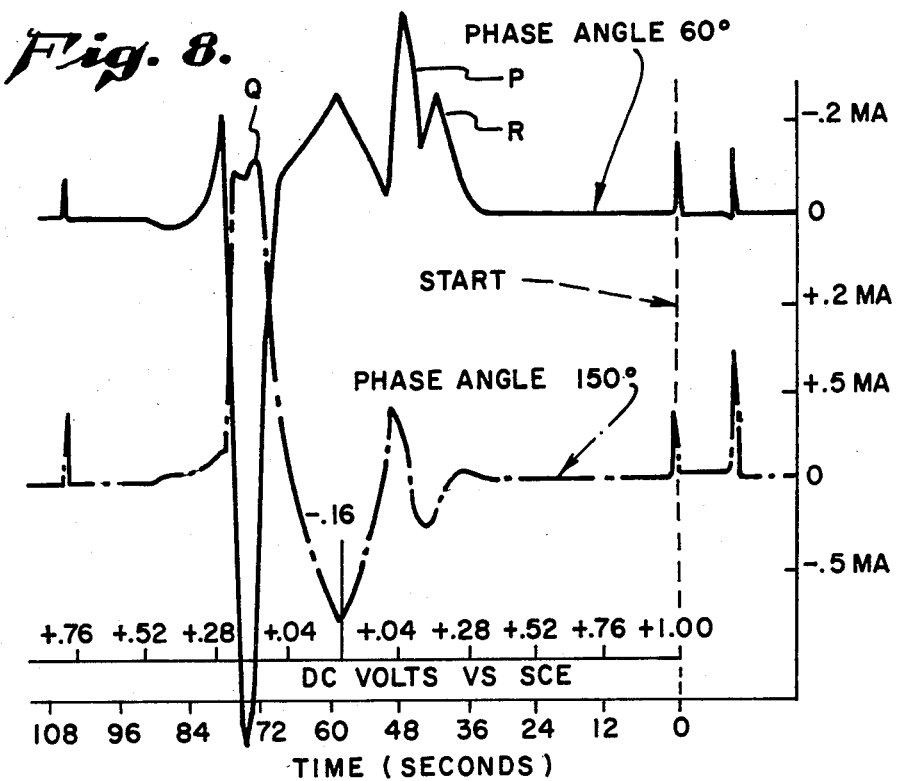

FIG. 8: Same as FIG. 2 bath except 5 ml/gal total (4.17 ml/gal "D", 0.83 ml/gal "Lo").

Figure 9:
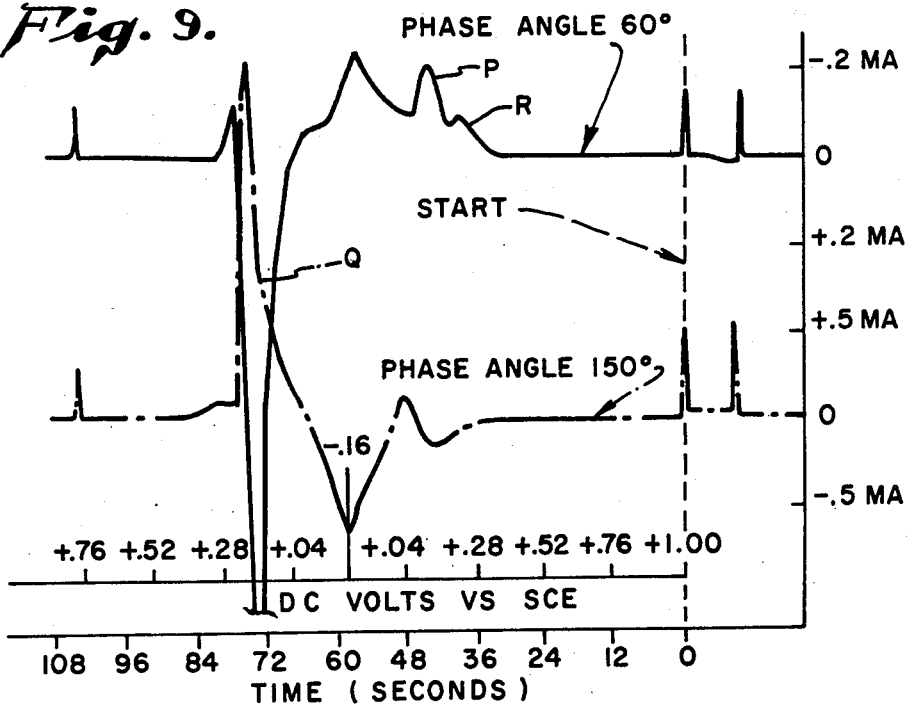

FIG. 9: Same as FIG. 2 bath except 20 ml/gal total (16.67 ml/gal "D", 3.33 ml/gal "Lo").

Figure 10:
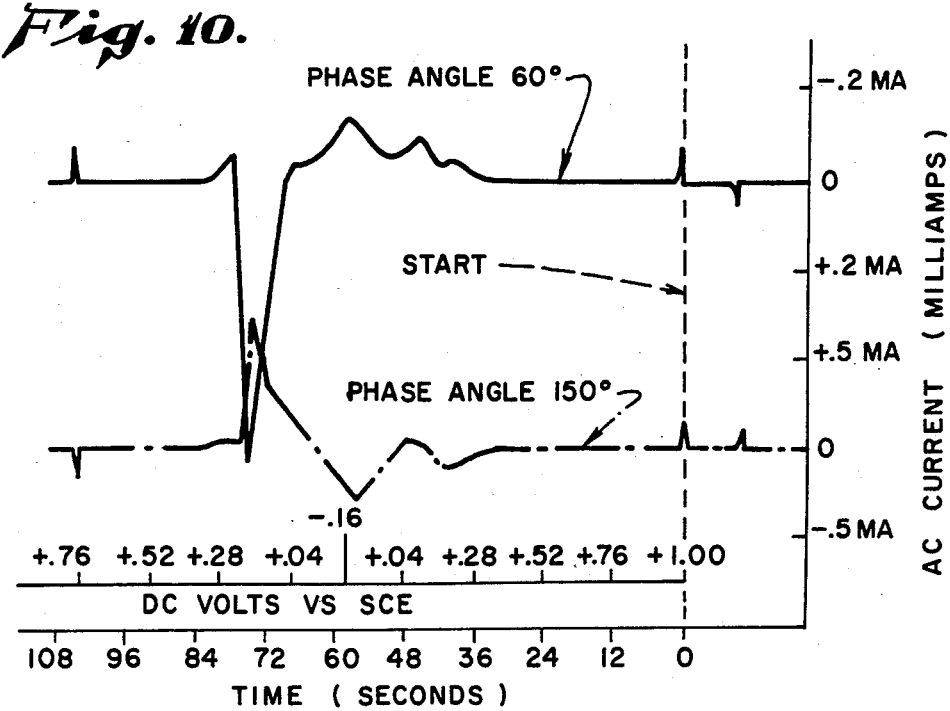

FIG. 10: Sel-Rex Cu-Bath M Special (caused 2.0% change in dimensions in thermal stability test)

Figure 11:
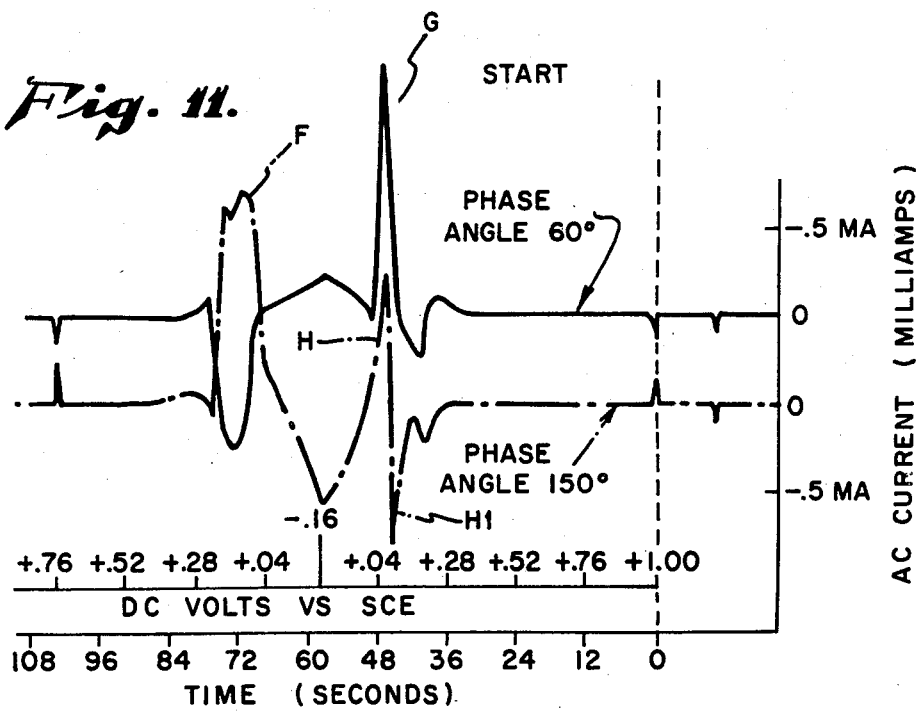

FIG. 11: Sel-Rex Cu-Bath M Special (caused 0.32% change in dimensions in thermal stability test).

The addition agent compositions in the baths for FIGS. 2-9 are summarized in Table 1 along with the effect the addition agents have on peak heights P, Q and R.

The spectra were measured at a 60° phase angle

The changes in the spectra due to additive level variations provides a useful method of monitoring the amounts of various additives in the plating bath.

TABLE 1

| | Addition Agent Calibration of Component D + Lo | | | |
|---|---|---|---|---|
| FIG. | Total D + Lo ml/gal | Ratio D/Lo | Peak Height Q (arbitrary units) | Peak Height P + R (arbitrary units) |
| 2 | 5 | 3 | 32 | 12.5 |
| 3 | 10 | 3 | 24 | 11.5 |
| 4 | 20 | 3 | 14 | 7.0 |
| 5 | 5 | 4 | 32 | 16.5 |
| 6 | 10 | 4 | 26 | 16.0 |
| 7 | 20 | 4 | 14 | 10.5 |
| 8 | 5 | 5 | 35 | 28.0 |
| 9 | 20 | 5 | 14 | 11.5 |

FIGS. 2-4 show that the best correlation with total additive is given by peak Q. Peaks P+R are a measure of the ratio of D and Lo. Note for example that peaks Q in FIGS. 4, 7 and 9, which all have 20 ml/gal total D+Lo, all have peak heights of 14 units. Note also the consistency in FIGS. 2, 5 and 8 which are all at about 32 units for peak Q but have values of 12.5, 16.5 and 28.0 for peaks P/R as D/Lo changes from 3 to 4 to 5.

Electroforms must be dimensionally stable. Temperature excursions were used to measure the dimensional stability of Sel-Rex Cu-Bath M Special plated electroforms. In FIG. 10, a 2.0% change in dimensions was obtained (i.e., hysteresis after return to original temperature). Excess of total addition agent appears to be related to the problem, as can be seen by comparison to FIG. 11 where a 0.3% dimensional change appears to relate to less total addition agent as evidenced by peak F (which corresponds to peak Q in Table 1 and FIGS. 2-9). The strong peaks at G and H, H[1] are believed to result from extensive working of the bath as well as an excessive ratio of D/Lo and are also a measure of the change in dimensional stability. In this way, dimensional stability can be related to the allowable concentration limits of each addition agent component. This capability is important since one component is used up much faster during production plating than the other component.

FIGS. 2-9 show only the effects of varying the addition agents. Calibration curves also have been determined for varying amounts of trace chloride, which has strong interactions with one of the additive components. Other calibrations involved acid and copper levels, which were shown to have only a small effect on some of the fingerprint peaks. Aging and working of the copper bath also causes some changes in the spectra. Calibration of these changes in terms of desired deposit properties can be used to keep a working bath at optimum performance as it ages.

Figure 12:
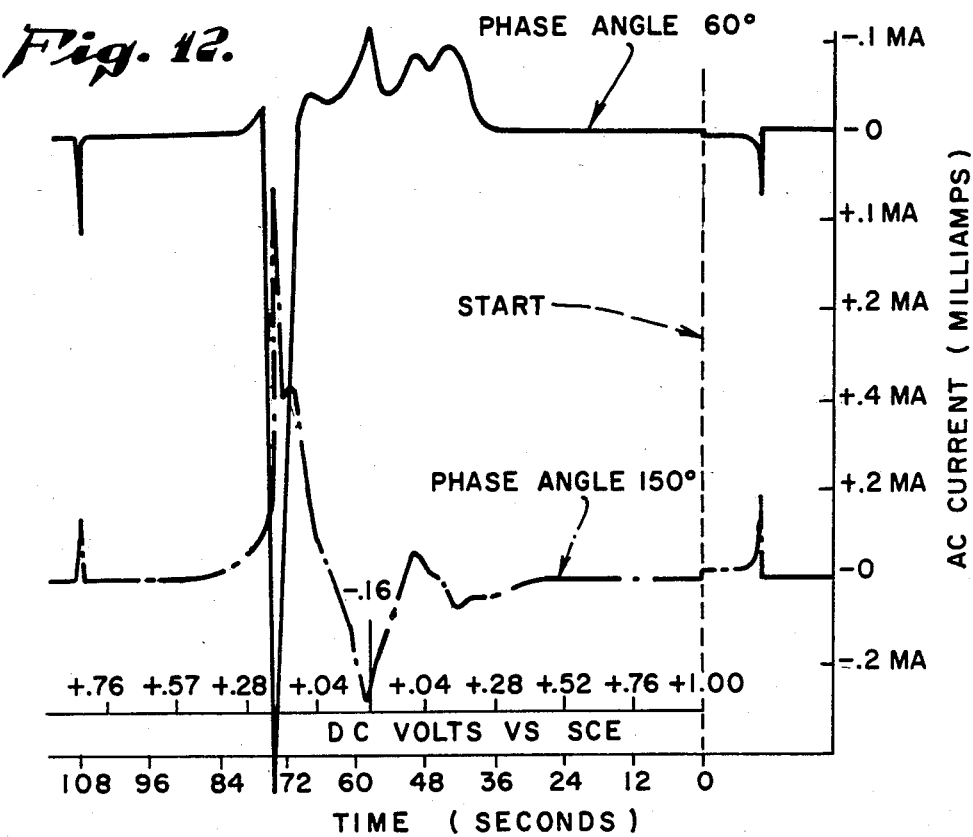
Figure 13:
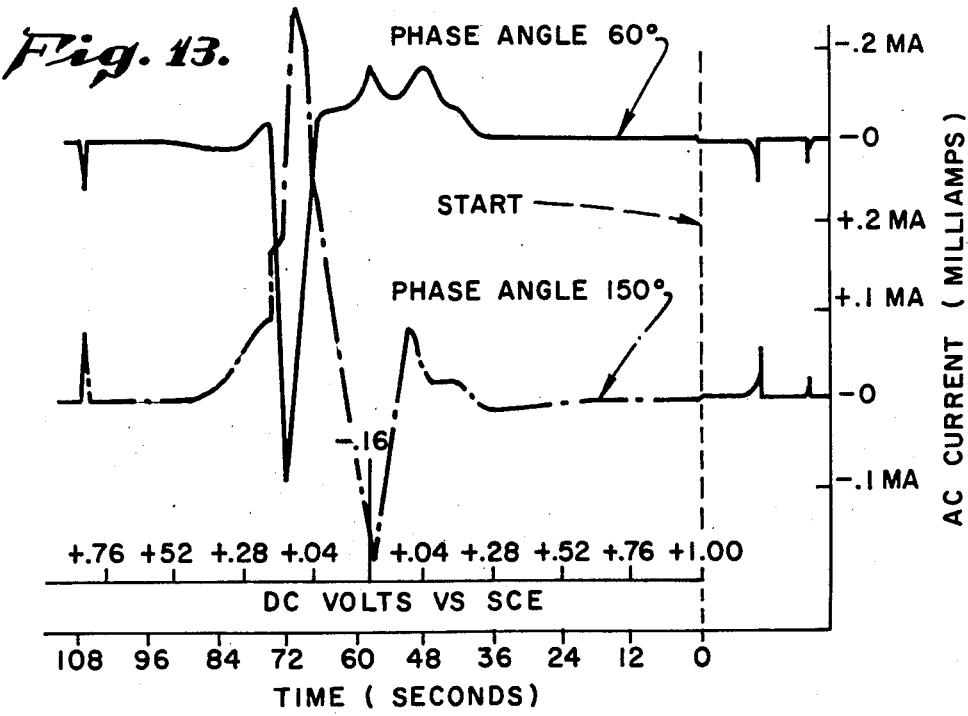

Low and high chloride spectra are shown in FIGS. 12 and 13 for a Lea Ronal Gleam PC acid copper bath which belongs to a different class of acid copper baths (category B, strong suppressor). The Lea Ronal Gleam PC bath was prepared according to the manufacturerW's instructions with proprietary ingredients available by Lea-Ronal Inc., 272 Buffalo Avenue, Freeport, N.Y. 11520. The FIG. 12 bath was a Lea-Ronal Copper Bath with 0.5 volume percent PC addition agent and 20 ppm $Cl^-$. The bath was pre-treated at +1.5 volts to maximize $Cl^-$ interactions with PC. The FIG. 13 bath was the same as the FIG. 12 bath except that the $Cl^-$ concentration was 100 ppm. The spectra are similar to the Sel-Rex spectra, but not identical. There are strong differences at other phase angles than 60°. The outlined method of finding the best fine structure reveals that fine structure spectra are optimized at different values of the various variables.

As can be seen by comparing the 150° phase angle peaks shown at 72 seconds in FIGS. 12 and 13, there is a strong interaction between the chloride ion and the addition agent which produces substantially different peaks at 72 seconds in the two spectra. These strong chloride interactions can be minimized by altering pretreatment procedures, as has been previously discussed. However, it is desirable to vary other parameters in order to avoid interactive interference effects altogether, so that straightforward calibrations of individual component concentrations can be made without interferences from other components. This variation was done for the Lea Ronal acid copper Gleam PC bath as illustrated in Table 2. Spectra were obtained in the same manner as for those shown in FIGS. 2-13. Peaks A-F in the spectra which appeared at various sweep times were chosen. Each of the bath constituents listed in the left column of Table 2 was systematically varied and the change in the various peaks A-F was noted. All peaks were determined within the normal range of plating bath concentrations. The electrodes were pretreated for 20 seconds at +1.5 volts vs. SCE (20° C.) with a dc sweep rate of 20 mV/sec and with an ac amplitude of 25 mV. N in Table 2 indicates that the peak was not affected by changes in the concentration of the ingredient (i.e. a non-sensitive peak). S in Table 2 indicates that the peak was sensitive to changes in concentration of the particular constituent or ingredient and that this peak can function as a diagnostic peak.

The negative limit of the dc potential range was extended to either −0.60 or −0.80 volts vs. SCE. The extended range produced extra peaks which an also be used for analysis of all the bath trace constituents. It was found that by using either of the electrode pretreatments mentioned previously, the spectra for the Lea Ronal bath were completely insensitive to variations in chloride concentration at 45° and 135° at 50 Hz and 400 Hz.

TABLE 2

| Second Harmonic Non-interactive Peaks For Lea Ronal Acid Copper Gleam PC Plating Baths | | | | | |
|---|---|---|---|---|---|
| | 50 Hz | | 400 Hz | 1500 Hz | |
| | 45/135° Peaks | | 45/135° Peak | 45/135° Peaks | 0/90° Peaks |
| Bath Constituent | A | B | C | D E | F |
| Chloride ion | N | N | N | S N | N |
| Addition Agent Constituent X | S | N | N | N S | N |
| Addition Agent Constituent Y | N | S | S | N N | N |

TABLE 2-continued

Second Harmonic Non-interactive Peaks
For Lea Ronal Acid Copper Gleam PC Plating Baths

| | 50 Hz | 400 Hz | 1500 Hz | | |
| | 45/135° Peaks | 45/135° Peak | 45/135° Peaks | | 0/90° Peaks |
| Bath Constituent | A | B | C | D | E | F |
|---|---|---|---|---|---|---|
| Addition Agent Constituent Z | N | N | N | N | N | S |
| 10% change in $H_2SO_4$ concentration | N | N | N | N | N | N |
| 10% change in $CuSO_4$ concentration | N | N | N | N | N | N |

However, at 1500 Hz and 45° and 135° reference phase angles, several spectral peaks were very sensitive to chloride ion concentrations between zero and 200 ppm. The Gleam PC was found to contain three separate addition agent constituents which are designated as "X", "Y", and "Z" in Table 2. By extending the sweep range to −0.60 volt it was found that addition agent constituent X concentration variations produced no spectral changes at 400° Hz. However, one peak changed substantially at 45° and 50 Hz. Also, several peaks changed at 1500 Hz, but they were different peaks than the chloride sensitive peaks. Variations in the concentration of addition agent constituent Y gave no spectral effects at 1500 Hz, but showed variations in specific peak heights at 45° and 400 Hz, especially when the sweeps were started at 0.4 volt vs. SCE rather than +1.0 volt. Specific peak heights at 45° and 50 Hz also varied, but these peaks were not the same peaks as those for addition agent constituent X. Finally, addition agent constituent Z showed no interaction for those peaks at 45° and 50 Hz, 400 Hz or 1500 Hz which were diagnostic for the other constituents, but did show diagnostic responses at 0° and 1500 Hz. None of the diagnostic spectra were sensitive to possible process variations in copper or sulfuric acid concentrations. All diagnostic responses were monotonic increasing or decreasing. It is important to note that each of the peaks listed in Table 2 was sensitive for one constituent only and therefore each peak provides a selective diagnostic indicator for one ingredient.

As is apparent from the previous discussion, in a bath where interactions occur between the numerous chemical species in the bath, quantitative analyses without interferences are possible (as shown in Table 2) for all bath trace components by extending the dc sweep range and/or using the reference phase angle and ac frequency as variables to find diagnostic responses without interferences. This may require that a number of different spectra be obtained at different values of the variables in order to perform a complete analysis. In this way all trace components (including chloride ion) of the Lea Ronal Gleam PC bath can be separately and quantitatively analyzed without interferences from each other or from the major bath constituents.

Other types of baths, for example acid cyanide gold baths, must be handled at different pretreatement voltages and dc sweep ranges to obtain diagnostic peaks. The gold can be swept as negatively as −1.0 volt vs. SCE, but should not be pretreated or swept more positive than +0.80 volt vs. SCE.

It has been found that the sweep range in the negative direction should be extended to that limit needed to develop those peaks required for analysis of desired trace constituents and to that limit required for the elimination of interferences. The prior guideline of a negative limit at which currents are 50–100 times the currents of the smallest peaks is negated when interferences are present. The only limit on the possible negative excursion to eliminate interferences is signal/noise ratio. For example, if the dc sweep limits are extended beyond about −0.8 volt for acid copper or −1.0 volt vs. SCE for acid gold, the signal/noise ratio decreases to undesirable levels. Undesirable levels for the signal/noise ratio are those below 5/1.

Returning to the discussion of the Sel-Rex bath, the additives are known to contain at least two trace materials which either directly or through their degradation products affect deposit properties. The changes in the spectra shown in FIGS. 2–11 appear to be in monotonic relation to the added amounts of the addition agents. It is believed that what is being measured is the perturbation of various hydrogen, chloride, double-layer charging, copper and copper chloride complex peaks by the additives. This is the type of plating bath monitoring which is desired since it provides a measurement of the actual effect of the trace materials on the copper deposit.

The figures show the spectra obtained when the ac current was measured at a phase angle of 60° relative to the ac signal source. Some of the peaks and nuances are better resolved at other relative phase angles. By varying the phase angle at which the spectra is obtained, it is believed that optimum spectra having the greatest number of peaks and resolution can be obtained. Spectra or fingerprints having more complex spectra and better peak resolution are capable of providing more information regarding the trace constituents and their affect on the plating deposit. This allows more accurate monitoring of changes in plating deposit characteristics caused by trace constituents. In addition, most addition agents are highly surface active and therefore should have a strong effect on the electrode double layer capacity. Some of the addition agents can be completely electroinactive, i.e., they are neither oxidized nor reduced. Accordingly, the only electrochemical signal these agents can give is a capacitive response. By varying the phase angle at which the ac current is measured, the spectra for these electroinactive compounds can be obtained. By making both in phase (i.e., 0° and 180°) and out of phase measurements of the ac current during the dc voltage sweep, spectra for both electroactive and electroinactive trace constituents can be obtained to provide a more complete picture of the quality of the plating bath than possible with prior dc voltammetric methods.

An important aspect of the present method is that the ac signal serves as a first derivative of the dc sweep. Therefore the large concentration of copper in the bath does not interfere with the fine structure and resolution of the trace constituents. The large copper concentration in essence serves as a nearly constant background signal on which the fluctuations of trace constituent fine structure waves are superposed. In order to obtain even better resolution, second harmonic ac (second derivative) measurements to suppress the major peaks even more and thereby to accentuate the fine structure may be taken. Second harmonic ac measurements involve measuring the ac current at twice the frequency of the ac source signal.

Working production bath samples were taken from a commercial plating bath and analyzed with the above-described exemplary system. From the spectra obtained, it could be seen that the production bath fit into the sequence of simulated plating baths tested in FIGS. 2-11.

It should be noted that the expected differences were observed between a new unworked (no plating has occurred) bath containing fresh addition agent, a new but worked bath (one in which plating has been done), and an old worked bath which has been idle for some time (loss of addition agent has taken place).

The spectra in the examples were obtained in an unstirred bath over an ambient air atmosphere at room temperature. The spectra were not altered when the solution was mildly stirred and agitated with a flow of nitrogen to replace the air, thus showing that the technique is insensitive to variations in the ambient environment. However, vigorous agitation diminishes sensitivity and fine structure resolution.

The method of the present invention, using first and second harmonic phase sensitive ac voltammetry, provides enhancement of spectral fine structure by means of a predetermined and systematic variation for optimum response of a large number of independent physical test variables. These include: 1) extent of dc range; 2) ac frequency; 3) ac amplitude; 4) dc sweep rate; 5) electrode pre-treatment; and 6) selection of one or more reference phase angles.

In regular dc cyclic voltammetry, small fine structure peaks are swamped by large peaks. It has not been previously known that these extra peaks exist. Whereas cyclic voltammetric stripping shows one, or at most two, stripping peaks, the method of the present invention provides at least seven. These peaks are related to the various components of the trace addition-agents. Furthermore, differences in the fine structure spectra provided by these peaks are related to differences in the deposit properties of the bath. Accordingly, the present invention provides a valuable method for accurately monitoring trace constituents present in plating baths to control plating quality.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein.

What is claimed is:

1. A method for monitoring the minor constituents present in a solution used in a plating process wherein said minor constituents affect plating deposit properties, said method comprising the steps of:
   (a) applying a selected dc potential to a working electrode which has been subjected to pretreatment and is positioned with said solution containing said minor constituents;
   (b) superimposing a constant ac signal on said dc potential applied to said working electrode, said ac signal having a peak to peak potential and a frequency and producing an ac current;
   (c) varying said dc potential at a chosen sweep rate over a chosen range; and
   (d) measuring said ac current at one or more phase angles with respect to said constant ac signal between said working electrode and a counter electrode positioned within said solution as said dc potential is varied over said range, said measurement of ac current in relation to varying dc potential being expressed as an ac current spectra wherein the improvement comprises varying in combination each parameter comprising said peak to peak potential of said ac signal, said frequency of said ac signal, said sweep rate of said dc potential, said range of dc potential, said one or more phase angles, and said pretreatment of said working electrode, to determine the specific value of each said parameter which, when taken in combination with the remaining said parameters, provides maximum spectra detail in said ac current spectra to determine and monitor said minor constituents in said solution which affect said plating deposit properties.

2. A method according to claim 1 wherein said plating bath solution includes a metal for plating a deposit and wherein said range over which said dc potential is varied includes a plating potential range in which said metal is plated onto said working electrode and a stripping potential range in which metal present on said working electrode is stripped therefrom.

3. A method according to claim 2 wherein said dc potential is varied from said stripping range to said plating range and then back to said stripping range.

4. A method according to claim 2 wherein said working electrode is subjected to said pretreatment prior to said applying of said dc potential to said working electrode, and said pretreatment comprises establishing equilibrium conditions surrounding said working electrode by stirring said plating bath solution for a first selected period of time and then allowing said plating bath solution to be quiescent for a second selected period of time, and subsequently anodically preconditioning and stabilizing said working electrode at a selected voltage or set of voltages positive to or within said sripping potential range for one or more selected periods of time to thereby maximize the reproducibility of said spectra detail of said ac current spectra.

5. A method according to claim 4 wherein the working electrode is anodically preconditioned at a voltage equal to or more positive than said selected voltage to maximize halide ion interaction or at a voltage less positive than said selected voltage to minimize halide interactions.

6. A method according to claim 1 wherein said range of said dc potential is extended to a negative voltage limit at which the ac current or the subsequent ac stripping current rises to approximately 50 to 100 times the current of the smallest peaks in said ac current spectra.

7. A method according to claim 1 wherein measurement of said ac current is made at the second harmonic frequency relative to the frequency of said ac signal to further maximize said spectra detail.

8. A method according to claim 7 wherein said range of said dc potential is extended to a negative limit at which the ac current or the subsequent ac stripping current rises to approximately 50 to 100 times the current of the smallest peaks in said ac current spectra.

9. A method according to claim 8 wherein said range of said dc potential is extended beyond said negative limit in order to avoid interferences between plating bath constituents or to develop extra peaks for analysis of all said minor constituents.

10. A method according to claim 9 wherein the negative limit is extended until the signal/noise ratio decreases to an undesirable level.

11. A method acccording to claim 10 wherein quantitative analyses of said minor constituents in said plating bath are obtained by determining two or more spectra for said minor constituents and wherein interferences are eliminated by varying the phase angle and ac frequency.

12. A method according to claim 1 wherein said plating bath solution includes a metal selected from the group consisting of copper, iron, nickel, chromium, zinc, tin, gold, silver, lead, platinum, cadmium, palladium, rhodium, indium, cobalt and mixtures thereof.

13. A method according to claim 12 wherein the dc potential is varied from about 1 millivolt/second to about 500 millivolts/second.

14. A method according to claim 13 wherein said metal is copper and said plating bath solution is acidic, and wherein the dc potential is varied at a rate of about 20 millivolts/second.

15. A method according to claim 12 wherein said ac signal has a peak to peak potential of between about 5 millivolts and 100 millivolts and a frequency of between about 10 hertz and 10,000 hertz.

16. A method according to claim 15 wherein said metal is copper and said plating bath solution is acidic, and wherein the peak to peak potential is about 25 millivolts and the frequency is about 50 hertz.

17. A method according to claim 12 wherein said metal is copper and said plating bath solution is acidic, and the range over which said dc potential is varied is between about +1.1 volts and −0.2 volt versus a standard calomel electrode.

18. A method for monitoring the change in minor constituents present in a plating bath solution which affect plating deposit properties, said method comprising the steps of:
   using the method of claim 1 to make a first determination of one or more ac current spectra for a plating bath solution having known desirable plating properties;
   using the method of claim 1 to make a second determination of one or more ac current spectra for said plating bath solution at a time after said first determination; and
   comparing said second spectra to said first spectra to monitor changes in the minor constituents present in the plating bath solution.

19. A method according to claim 1 wherein the following steps are performed in turn:

(a) the value of each of said parameters is set at a predetermined level;
(b) the value of a first said parameter is varied in order to determine and set a specific value of said first parameter which optimizes the detail in said ac current spectra;
(c) the value of a second said parameter is varied in order to determine and set a specific value of said second parameter which optimizes the detail in said ac current spectra; and
(d) the value of each remaining said parameter, in turn, is varied in order to determine and set the specific value of each said remaining parameters which optimizes the detail in said ac current spectra wherein said specific values of said parameters, when taken in combination, provide said miximum spectra detail.

20. In a cyclic voltammetric stripping method for monitoring the presence of minor constituents in a metal plating bath solution wherein: (a) a dc potential is applied to a pretreated working electrode immersed in said plating bath solution and said dc potential is cycled at a constant sweep rate over a chosen range so that a small amount of said metal is alternately deposited on the surface of said working electrode by electrodeposition and stripped off by anodic dissolution; (b) a constant ac signal is superimposed on said dc potential applied to working electrode, said ac signal having a chosen peak to peak potential and a chosen frequency and producing an ac current; (c) measuring said ac current at one or more phase angles with respect to said constant ac signal between said working electrdoe and a counter electrode positioned within said plating bath solution as said dc potential is cycled, said measurement of said ac current in relation to said cycled dc potential being expressed as an ac current spectra of said plating bath solution wherein the improvement comprises varying in combination each parameter comprising said peak to peak potential of said ac signal said frequency of said ac signal, said sweep rate of said dc potential, said range of said dc potential, said one or more phase angles, and said pretreatment of said working electrode to determine the specific value of each said parameter which, when taken in combination with the remaining said parameters, provides maximum spectra detail in said ac current spectra to determine and monitor said minor constituents present in said plating bath solution.

21. An improved method according to claim 20 wherein measurement of said ac current is made at the second harmonic frequency of said ac signal.

* * * * *

UNITED STATES PATENT AND TRADEMARK OFFICE
CERTIFICATE OF CORRECTION

PATENT NO. : 4,631,116

DATED : December 23, 1986

INVENTOR(S) : Frank A. Ludwig

Page 1 of 2

It is certified that error appears in the above—identified patent and that said Letters Patent is hereby corrected as shown below:

Col. 11, line 6, after "test)" insert --.-- (a period).
　　　　　line 13, after "angle", insert
　　　　　-- relative to the source ac signal, with the quadrature spectra also being obtained. As can be seen, some of the spectra peaks are depressed, some enhanced and others unaltered by the various levels of additives. --

Col. 13, line 30, before "0.4", insert -- + -- (a plus sign).

Col. 16, line 7, after "of" insert -- said --.

Col. 18, line 16, delete "miximum" and insert therefor -- maximum --.
　　　　　line 28, after "to" insert -- said --.
　　　　　line 32, delete "electrdoe" and insert therefor -- electrode --.

UNITED STATES PATENT AND TRADEMARK OFFICE
CERTIFICATE OF CORRECTION

PATENT NO. : 4,631,116

DATED : December 23, 1986

INVENTOR(S) : Frank A. Ludwig

It is certified that error appears in the above-identified patent and that said Letters Patent is hereby corrected as shown below:

Column 18, line 39, after "signal" insert -- , --. ( a comma).

Signed and Sealed this

Twenty-second Day of December, 1987

Attest:

DONALD J. QUIGG

Attesting Officer

Commissioner of Patents and Trademarks